(12) United States Patent
Conway et al.

(10) Patent No.: US 10,894,007 B2
(45) Date of Patent: Jan. 19, 2021

(54) HAIR CARE COMPOSITION WITH ENCAPSULATED MOISTURIZERS AND METHOD TO DELIVER EXTENDED MOISTURE RELEASE TO THE HAIR

(71) Applicants: Henkel IP & Holding GmbH, Duesseldorf (DE); Henkel (China) Investment Co., Ltd., Shanghai (CN)

(72) Inventors: Mary J Conway, Phoenix, AZ (US); Jisook Baek, Shanghai (CN)

(73) Assignees: Henkel IP & Holding GmbH, Duesseldorf (DE); Henkel (China) Investment Co., Ltd., Shanghai (CN)

( * ) Notice: Subject to any disclaimer, the term of this patent is extended or adjusted under 35 U.S.C. 154(b) by 22 days.

(21) Appl. No.: 15/723,655

(22) Filed: Oct. 3, 2017

(65) Prior Publication Data

US 2018/0110699 A1    Apr. 26, 2018

(30) Foreign Application Priority Data

Oct. 26, 2016 (CN) .......................... 2016 1 0942398

(51) Int. Cl.
| | | |
|---|---|---|
| *A61K 8/11* | (2006.01) | |
| *A61K 8/39* | (2006.01) | |
| *A61K 8/34* | (2006.01) | |
| *A61K 8/37* | (2006.01) | |
| *A61K 8/44* | (2006.01) | |
| *A61K 8/891* | (2006.01) | |
| *A61K 8/46* | (2006.01) | |
| *A61K 8/81* | (2006.01) | |
| *A61K 8/41* | (2006.01) | |
| *A45D 34/00* | (2006.01) | |
| *A61Q 5/00* | (2006.01) | |
| *A61Q 5/02* | (2006.01) | |
| *A61Q 5/06* | (2006.01) | |
| *A61Q 5/12* | (2006.01) | |

(52) U.S. Cl.
CPC ................ *A61K 8/11* (2013.01); *A45D 34/00* (2013.01); *A61K 8/342* (2013.01); *A61K 8/37* (2013.01); *A61K 8/375* (2013.01); *A61K 8/39* (2013.01); *A61K 8/416* (2013.01); *A61K 8/44* (2013.01); *A61K 8/463* (2013.01); *A61K 8/817* (2013.01); *A61K 8/891* (2013.01); *A61Q 5/00* (2013.01); *A61Q 5/002* (2013.01); *A61Q 5/02* (2013.01); *A61Q 5/06* (2013.01); *A61Q 5/12* (2013.01); *A45D 2200/054* (2013.01); *A61K 2800/56* (2013.01); *A61K 2800/596* (2013.01); *A61K 2800/805* (2013.01)

(58) Field of Classification Search
None
See application file for complete search history.

(56) References Cited

U.S. PATENT DOCUMENTS

| | | |
|---|---|---|
| 6,171,537 B1 | 1/2001 | Cohen |
| 8,119,587 B2 | 2/2012 | Cavin et al. |
| 8,257,832 B2 | 9/2012 | Wilhelm et al. |
| 8,357,651 B2 | 1/2013 | Quellet et al. |
| 8,460,758 B2 | 6/2013 | Flood et al. |
| 8,846,198 B2 | 9/2014 | Buchner et al. |
| 2009/0291056 A1* | 11/2009 | Castro ............... A61K 8/06 424/70.7 |
| 2012/0276031 A1* | 11/2012 | Wei .................. A61K 8/0245 424/63 |
| 2014/0252312 A1 | 9/2014 | Lumb et al. |
| 2014/0312278 A1 | 10/2014 | Park et al. |
| 2014/0322283 A1 | 10/2014 | Berthier et al. |
| 2016/0166480 A1* | 6/2016 | Lei .................. C11D 17/0039 424/401 |

* cited by examiner

*Primary Examiner* — David J Blanchard
*Assistant Examiner* — Sarah J Chickos
(74) *Attorney, Agent, or Firm* — James J. Cummings

(57) ABSTRACT

Methods and composition are provided for a hair care composition that comprises at least one encapsulated moisturizing ingredient. The composition comprises at least one surfactant, at least one capsule that encapsulates a benefit agent, and a carrier. The composition may further comprise additional components, which may be a function of the type of hair care composition. A method of using a hair care composition that comprises at least one encapsulated moisturizing ingredient is also provided.

15 Claims, 4 Drawing Sheets

HAIR CARE COMPOSITION WITH ENCAPSULATED MOISTURIZERS AND METHOD TO DELIVER EXTENDED MOISTURE RELEASE TO THE HAIR

FIELD OF THE INVENTION

The present invention generally relates to hair care compositions, and more particularly relates to hair care compositions that comprise an encapsulated benefit agent to deliver extended release of the benefit agent to the hair.

BACKGROUND OF THE INVENTION

Hair care compositions are used to style, cleanse and provide a pleasant feel to the hair. Such compositions come in a variety of forms, and include shampoos, conditioners, leave-on conditioning sprays and styling products.

Some hair care compositions, such as shampoos, are used to cleanse the hair. Shampoos typically contain surfactants, which assist in the removal of excess oils from the hair. However, shampoos may remove too much oil from the hair, leaving the hair dry or brittle. Moisturizing ingredients can be included in such a cleansing composition; however, the majority of these moisturizing ingredients are washed away with the cleansing composition. Providing an encapsulated benefit agent may deliver extended release of the benefit agent, which may include a moisturizing ingredient that can be delivered to the hair after the bulk of the composition is washed away from the hair. Alternatively, the encapsulated benefit agent may include a conditioner, which may be delivered to condition the hair after the bulk of the composition is washed away from the hair. The encapsulated benefit agent may also provide an illuminating ingredients to the hair after the bulk of the composition has been washed away to improve the overall appearance of the hair.

Other hair care compositions, such as conditioners, are used to moisturize and condition the hair, to restore some of the moisture that was removed by a cleansing or shampoo composition. Such compositions may include conditioning agents, which act to retain moisture in the hair by a variety of mechanisms. Some conditioning agents, such as dimethicone, form a barrier and act to prevent the evaporation of moisture from the hair. Other agents, such as propylene glycol, act as humectants to attract moisture to the hair. In each case, the benefit persists only as long as the benefit agent is present on the hair. As such, providing an encapsulated benefit agent may provide increased benefits to hair feel and appearance by providing an extended release of the benefit agent by continuing to deposit the benefit agent onto the hair as the hair is touched, combed, brushed, or otherwise manipulated.

Additional hair care compositions are leave-in compositions. These include styling gels, hairsprays, creams, pomades, or waxes. Such compositions may also include benefit agents, such as moisturizing ingredients, conditioning ingredients, and illuminating ingredients. These benefit agents act immediately upon contact with the hair, but may decrease in efficacy over time. As a result, providing an encapsulated benefit agent may assist the benefit agent to provide increased benefit to hair feel and appearance by providing a gradual deposit of the benefit agent onto the hair as the hair is physically manipulated and the capsules are opened, releasing the benefit agent onto the hair.

Accordingly, it is desirable to provide a hair care composition that includes an encapsulated benefit agent. In addition, it is desirable to provide a hair care composition that can deposit an encapsulated benefit agent onto the hair because an extended release profile allows the benefit agent to provide increased benefits to the hair's softness, shininess, and overall healthy appearance. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A hair care composition is provided for extended release of a benefit agent onto the hair. The composition includes at least one surfactant selected from anionic, nonionic, zwitterionic and amphoteric surfactants, and also comprises at least one capsule, wherein the capsule encapsulates a benefit agent and the benefit agent provides at least 85% of the weight of the capsule. The hair care composition also includes a carrier.

A hair styling composition is provided for styling the hair and providing extended release of a benefit agent. The hair styling composition includes at least one capsule, that includes a capsule shell and a capsule core that contains water and at least one benefit agent. The hair styling composition also includes a carrier.

A method is provided for using a hair care composition comprising a capsule that contains an encapsulated benefit agent. The method includes applying the hair care composition that includes at least one capsule to the hair. The method also includes contacting the hair to open at least one capsule containing an encapsulated benefit agent, and depositing the benefit agent onto the hair.

BRIEF DESCRIPTION OF THE DRAWINGS

The present invention will hereinafter be described in conjunction with the following drawing figures, wherein like numerals denote like elements, and FIG. 1A is a diagram of an intact capsule containing a benefit agent according to an example of the principles described herein;

FIG. 1B is a cross-sectional diagram of the capsule of FIG. 1A, including the benefit agent contained within the capsule, according to an example of the principles described herein;

DETAILED DESCRIPTION OF THE INVENTION

Figure 1C:
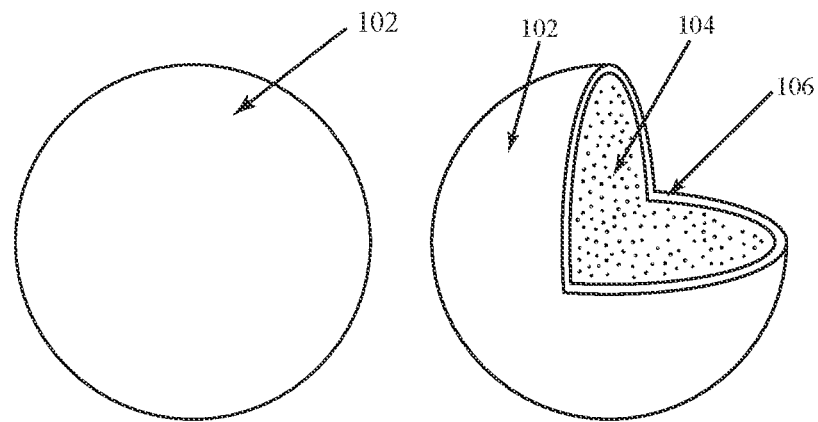
FIG. 1C shows an another example of a capsule holding an encapsulated benefit agent, wherein the capsule is porous to gradually release the benefit agent from an intact capsule, according to an example of the principles described herein.

The following detailed description of the invention is merely exemplary in nature and is not intended to limit the invention or the application and uses of the invention. Furthermore, there is no intention to be bound by any theory presented in the preceding background of the invention or the following detailed description of the invention.

As used herein, the term "about" refers to amounts, concentrations or values that are within 10 percent of the expressed amount, concentration or value. Additionally, all provided concentration ranges are intended to include all possible concentration ranges contained within the provided range.

As noted above, providing a hair care composition that comprises an encapsulated benefit agent may provide hair that is treated with the composition with lasting benefits by providing an extended release profile for the benefit agent. Such an extended release profile allows the benefit agent to be provided to the hair after the bulk of the composition has been washed away from the hair, whereby providing the hair with increased shine, softness, and healthy appearance.

Compositions according to the present specification include an encapsulated benefit agent. The encapsulated benefit agent is a benefit agent that is contained within a capsule. The capsules may take a variety of forms, as will be discussed further below. The capsules may also contain additional components, such as fragrances to provide the user with a sensory awareness that the benefit agent has been released. The capsules may be designed to either open upon physical abrasion or to gradually release the benefit agent through pores in the surface of the capsule; these will be discussed further below.

The present specification also includes a method of using a composition that comprises an encapsulated benefit agent. The method includes applying the hair care composition that comprises an encapsulated benefit agent onto the hair, contacting the hair to open the capsules that contain the encapsulated benefit agent, and depositing the benefit agent onto the hair.

In one example, the method of using a composition according to the present specification also includes rinsing the composition from the hair, which leaves behind some of the capsules containing an encapsulated benefit agent. The encapsulated benefit agent is then released when the capsules that remain on the hair are opened by contacting the hair. In another example, the method of using a composition according to the present specification does not include rinsing the composition from the hair; this method is used for treatments such as hair sprays, pomades, and waxes.

The present specification also includes a method of making a composition that comprises an encapsulated benefit agent. The method includes preparing an aqueous slurry that contains a benefit agent to be encapsulated, and forming polymeric capsules in the aqueous slurry around the benefit agent.

In one example, the method of making a composition that comprises an encapsulated benefit agent further includes isolating the capsules from the aqueous slurry and adding the isolated capsules to a hair care composition. In another example, the method of making a composition that comprises an encapsulated benefit agent further includes adding additional hair care composition components to the aqueous slurry containing the encapsulated benefit agent, to produce a hair care composition that comprises an encapsulated benefit agent.

Figure 1C:
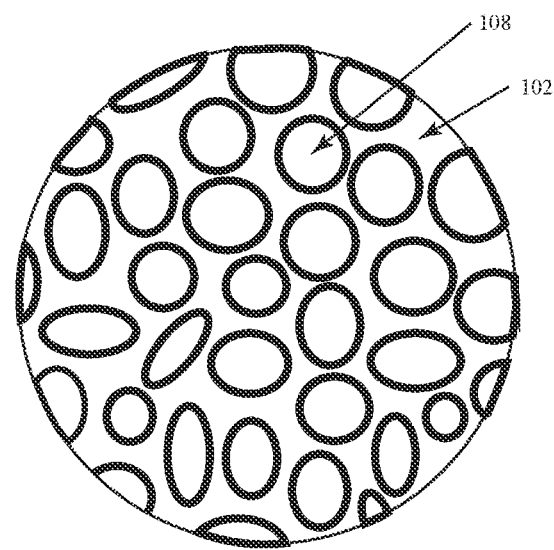

Turning now to the figures, FIG. 1 shows three diagrams of a capsule containing an encapsulated benefit agent. FIG. 1A shows an intact capsule (102) containing an encapsulated benefit agent. FIG. 1B shows a cross-section of a capsule (102) that shows the encapsulated benefit agent (104) contained within the shell (106) of the capsule (102). FIG. 1C shows an alternate form of the capsule (102), in which the capsule includes pores (108) that allow for the release of the benefit agent (104) from the capsule (102).

Figure 2:
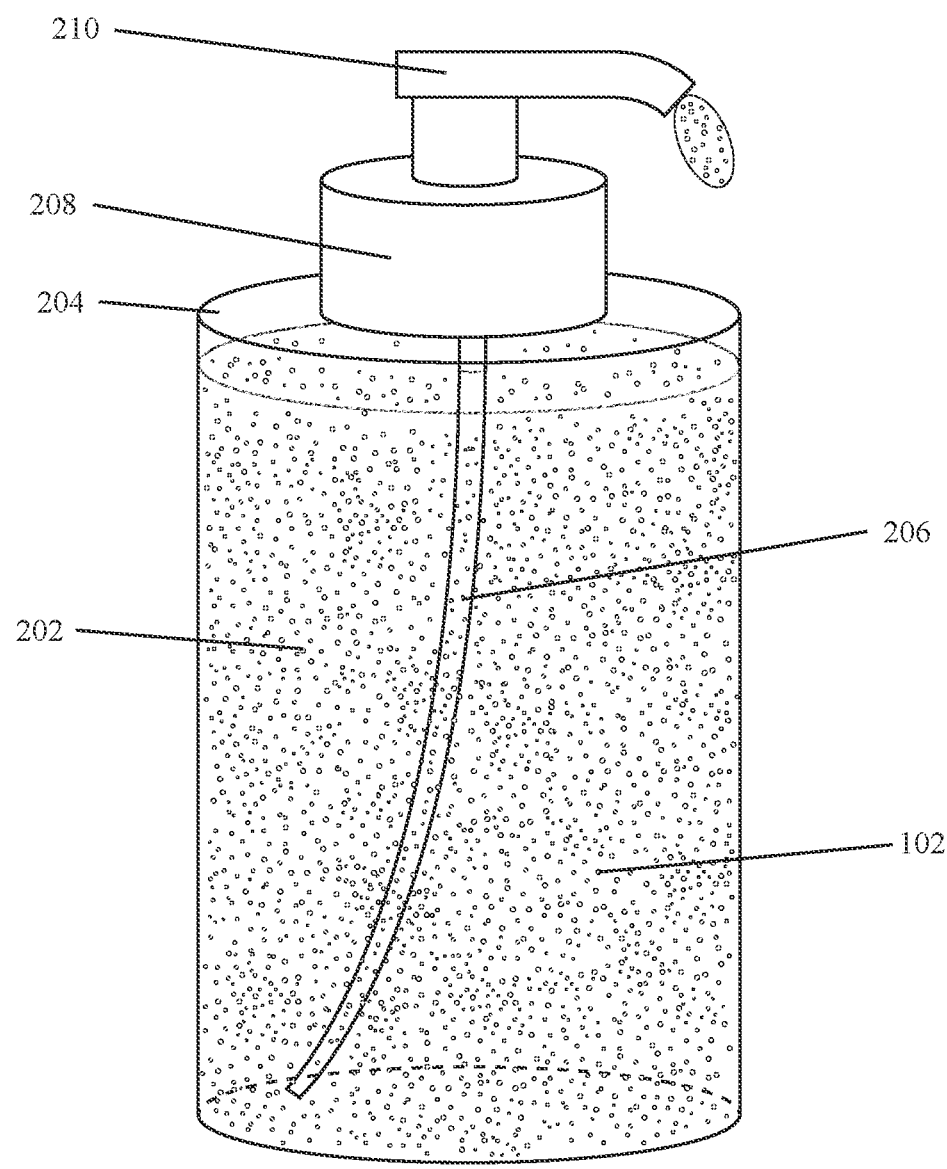
FIG. 2 shows a hair care composition according to the present specification in a container that is equipped with a pump-action dispensing mechanism, according to an example of the principles described herein.
Figure 3:
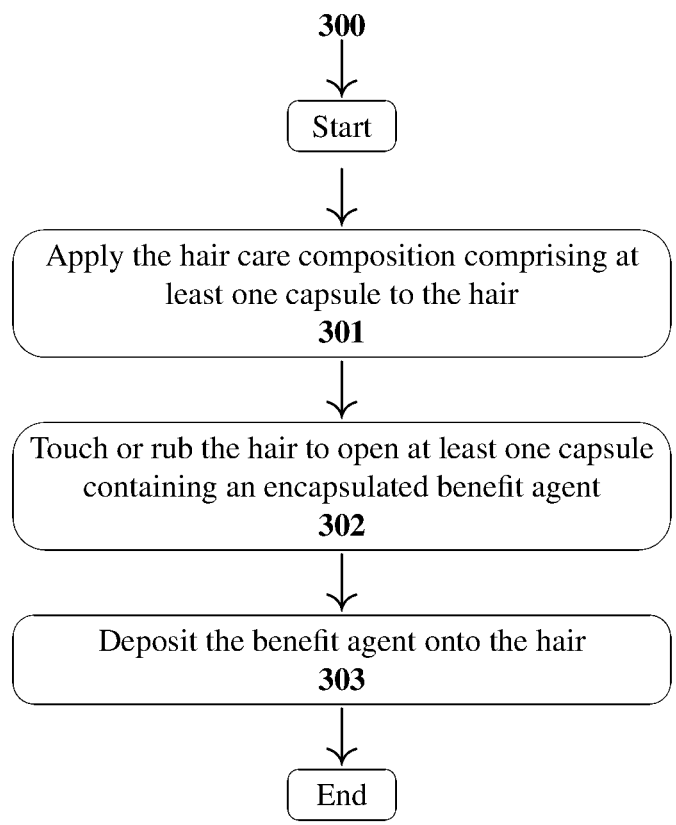
FIG. 3 is a flowchart of a method for using a hair care composition comprising an encapsulated benefit agent, according to an example of the principles described herein.
Figure 4:
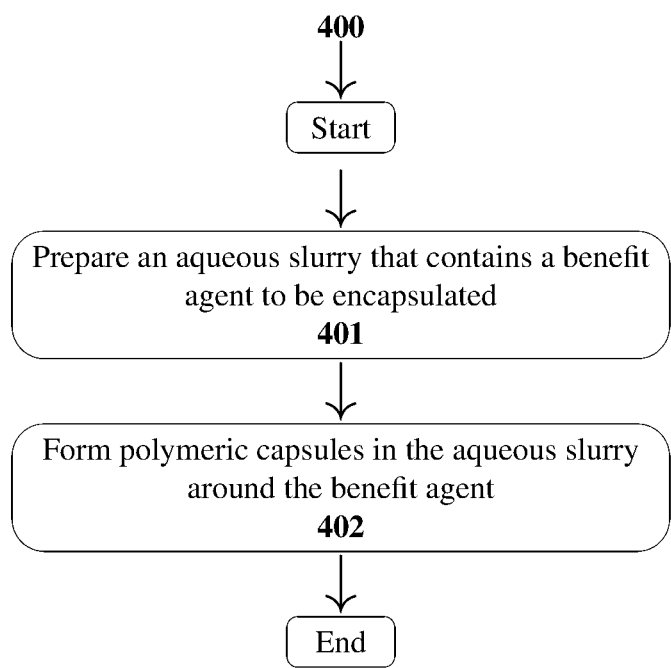
FIG. 4 is a flowchart of a method for making a hair care composition comprising an encapsulated benefit agent, according to an example of the principles described herein.

FIG. 2 shows a hair care composition (202) provided in a container (204) equipped with a dispensing mechanism (208). The capsules (102) containing the benefit agent (104) are also shown, although the capsules themselves may or may not be visible in the composition (202). In the example shown in FIG. 2, the dispensing mechanism (208) includes a dip tube (206) and a pump-actuator (210).

The capsule (102) encapsulates the benefit agent (104). The capsule (102) may be of any suitable size. The size of the capsule is measured as the longest straight line between one point on the surface of the capsule (102) and another point on the surface of the capsule (102). Equivalently, the size may also be expressed as the diameter of the smallest sphere that could surround the capsule (102). For a spherical capsule (102), the size of the capsule would be the diameter. For a cubical capsule (102), the size of the capsule would be the distance between two vertices on opposite ends of the capsule (102). For example, the capsule (102) may have a size ranging from about 1 micrometer ($\mu$m) to about 150 $\mu$m, such as from about 5 $\mu$m to about 75 $\mu$m, or from about 10 $\mu$m to about 50 $\mu$m. In another example, the capsule (102) may have a size ranging from about 10 $\mu$m to about 30 $\mu$m. It is not necessary that every capsule (102) within a composition (202) according to the present specification have a size within the provided range. Rather, the capsules (102) may have a variety of size distributions, including normal distributions, uniform distributions, or any other appropriate type of size distribution. The provided size ranges are intended to describe about 90% of the capsules (102) within the hair care composition (202).

A capsule (102) according to the present specification may have a shell (106) that has a thickness. For the purposes of the present specification, the thickness of the shell (106) is taken to be the average thickness of the surface of the shell (106), averaged by the surface area of the shell (106). The appropriate thickness of the shell (106) may depend on the nature of the polymer used to prepare the shell (106), as well as the structure of the shell relative to the benefit agent (104) contained within the capsule (102). A shell (106) of a capsule (102) according to the present specification may be of any suitable thickness. In one example, a capsule (102) according to the present specification may have a shell (106) with a thickness ranging from about 0.001 $\mu$m to about 75 $\mu$m. In another example, a capsule (102) according to the present specification may have a shell (106) with a thickness ranging from about 0.001 $\mu$m to about 5 $\mu$m thick, such as from about 0.01 $\mu$m to about 1 $\mu$m thick. In a further example, a capsule (102) according to the present specification may have a shell (106) with a thickness ranging from about 0.01 $\mu$m thick to about 2 $\mu$m thick, such as from about 0.02 $\mu$m to about 0.1 $\mu$m thick. In a further example, a capsule (102) according to the present specification may have a shell (106) with a thickness ranging from about 5 $\mu$m to about 75 $\mu$m thick, such as from about 10 $\mu$m to about 35 $\mu$m thick.

In one example, a capsule (102) according to the present specification may be visible by the human eye, unaided by mechanical or optical equipment. In another example, a capsule (102) according to the present specification may not be visible by the human eye, unaided by mechanical or optical equipment. In a third example, a composition (202) according to the present specification may contain both capsules (102) that are visible to the human eye, and capsules (102) that are not visible to the human eye, unaided by mechanical or optical equipment. A situation such as the third example may arise due to some variation in the size distribution of the capsules (102) according to the present specification.

The capsule (102) may take a variety of forms. Different forms of the capsule (102) may dispense the encapsulated benefit agent (104) onto the hair by different mechanisms. Different forms of the capsule (102) may be especially suitable for some types of hair care compositions, while other forms of the capsule (102) are suitable for other types of hair care compositions.

In one example, the capsule (102) completely encapsulates the benefit agent (104). If the capsule (102) completely encapsulates the benefit agent (104), then the benefit agent (104) is released by rupture of the capsule (102). Such a rupture of the capsule (102) may be effectuated by physical abrasion on the capsule (102), which occurs when the hair is brushed, combed, or otherwise physically manipulated, such as by the user's hand. Premature rupture of the capsule (102), such as by the abrasion in the application of the composition (202) to the hair, is mitigated by the composition of the capsule (102), discussed further below. A type of capsule (102) that releases the benefit agent (104) by abrasion-induced rupture of the capsule (102) may be used for any type of hair care composition (202), but may be especially suitable for hair care compositions (202) that are intended to leave the hair malleable, such as shampoos and conditioners.

In another example, the capsule (102) includes pores (108); this example is shown in FIG. 1C. In such an example, it is not necessary for the capsule (102) to rupture to release the benefit agent (104) onto the hair because the benefit agent (104) can be gradually released through the pores (108) on the capsule (102). If the capsule (102) contains pores (108), the size of the pores (108) may be optimized based on the release profile of the benefit agent (104) from the capsule (102). The size of the pores (108) is large enough to allow the benefit agent (104) to exit the capsule (102), but small enough to retain the benefit agent (104) within the capsule during storage and use. A type of capsule (102) that releases the benefit agent (104) by gradual diffusion through pores (108) may be used for any type of hair care composition (202), but may be especially suitable for hair care compositions (202) that are applied as hair fixatives, such as hairsprays, pomades and waxes.

In yet another example, the capsule (102) comprises a swellable crosslinked polymer matrix. The polymer matrix of the capsule (102) is impregnated with the benefit agent (104) during the preparation of the capsule (102), and the level of crosslinking is sufficiently high to retain the benefit agent (104) within the capsule (102) during storage. After application of the hair care composition (202) to the hair, the capsules (102) that remain on the hair gradually dry with the hair that surrounds the capsules (102). As the environment around capsules (102) dries, the swellable crosslinked polymer matrix of the capsule (102) shrinks, and the compressive force of this shrinking releases the benefit agent (104) onto the hair surrounding the capsule (102). A type of capsule (102) that releases the benefit agent (104) by drying of the surrounding environment resulting in de-swelling of a crosslinked polymer matrix of the capsule (102) may be used for any type of hair care composition (202), including shampoos, conditioners, hairsprays, pomades and waxes.

The capsule (102) includes a polymer. The polymer of the capsule (102) may provide an outer shell (106) to the capsule (102) to contain a benefit agent (104). Alternatively, the polymer of the capsule (102) may provide a crosslinked matrix that is impregnated with the benefit agent (104); such a crosslinked matrix may be assembled as an outer shell (106) with a continuous surface, an outer shell (106) that contains pores (108), or as a swellable crosslinked polymer matrix.

The polymer of the capsule (102) may be natural, semi-synthetic or synthetic. Suitable natural polymers include, for example, proteins, such as those similar to viral capsids or capsules assembled from clathrin or clathrin-related proteins. Hydrogels may be used as another form of encapsulation, and may be either natural or semi synthetic.

Synthetic polymers may be used to form the capsule (102) that encapsulates the benefit agent (104). Any suitable synthetic polymer may be used. Non-limiting examples of suitable synthetic polymers which may be used in a capsule (102) according to the present specification include (1) hexamethylenediamine/MDI copolymer, polyquaternium-6, acrylates copolymer, citric acid, and polyvinylpyrrolidone; (2) guanidine carbonate/HDI isocyanurate trimer/MDI crosspolymer, xanthan gum, polyvinyl alcohol, and guanidine carbonate; (3) polyurethane crosspolymer-2; and (4) combinations thereof. In some examples, a polymeric capsule (102) may be formed from monomeric units around a benefit agent (104). In other examples, a polymeric capsule (102) may be formed around a benefit agent (104) from polymeric and monomeric units, or from polymeric units.

In some examples, the polymer used to form the capsule (102) may also provide a styling benefit to the hair, either before or after the capsule (102) releases the benefit agent (104). For example, polyurethane polymers may be used as styling aids, and the capsule itself may provide a styling benefit to the hair.

In some instances, it may be advantageous for the polymer that provides the shell (106) of the capsule (102) to have a surface charge. Such a surface charge can assist the capsule to attach to the hair, and can assist the retention of the capsule when the bulk composition (202) is washed away for rinse-off type compositions (202), such as shampoos and conditioners. Any surface charge on the shell (106) of the capsule (102) may be used in a composition (202) according to the present specification. In one example, a composition (202) according to the present specification includes a capsule (102) with a positive charge on its surface which promotes attachment to the hair or skin. In another example, a composition (202) according to the present specification includes a capsule (102) with a negative charge on its surface, which may be combined in some examples with a cationic compound or polymer in the composition (202) to promote attachment to the hair or skin. In a further example, a composition (202) according to the present specification includes a capsule (102) with both positive and negative charges on its surface. In a still further example, a composition (202) according to the present specification includes a capsule (102) that is nonionic, and does not bear a surface charge.

A capsule (102) according to the present specification may be configured or designed so as to not release its contents prematurely. The capsule (102) according to the present specification may be sensitive to dryness of the surrounding environment, so that when the surrounding environment is moist, the shell (106) of the capsule (102) is relatively flexible, and does not easily rupture; however, when the surrounding environment is dry, the shell (106) of the capsule (102) may become more brittle, so that the capsule is more easily ruptured to release the benefit agent (104) contained therein. Such a design ensures that the capsule does not prematurely rupture when the composition (202) containing the capsule (102) is applied to the hair, or while the hair is being lathered, rinsed, styled, or otherwise processed; instead, the capsule (102) may be configured so that the capsule (102) only ruptures when the benefit agent (104) contained therein would provide a benefit to the hair that is not already being provided by the bulk composition (202).

Another type of capsule (102) may be configured to not rupture, but instead to gradually release a benefit agent (104) as the capsule (102) equilibrates with the surrounding environment and decreases in size as the hair surrounding the capsule dries. Such a capsule (102) may have pores (108), and may be prepared from a moisture-sensitive polymer.

The capsule may be formed in an aqueous environment. In one example, formation or assembly of the shell (106) of the capsule (102) around the benefit agent (104) may be triggered from the component pieces of the shell (106) of the capsule (102) by chemical means, such as by introduction of a catalyst to drive polymerization of the shell (106). In another example, formation or assembly of the shell (106) of the capsule (102) around the benefit agent (104) may be triggered from the component pieces of the shell (106) of the capsule (102) by a shift in the pH of the surrounding environment; in this example, capsule formation may be triggered either by a basic shift (from a lower pH to a higher pH) or an acidic shift (from a higher pH to a lower pH).

In addition to the benefit agent (104), a capsule (102) according to the present specification may also encapsulate additional elements. Such additional elements may include fragrance ingredients, vitamins, and any other ingredient for which an extended release profile provides a benefit to the hair. The co-encapsulation of a fragrance ingredient may be especially suitable. Co-encapsulation of a fragrance ingredient allows contemporaneous release of the fragrance ingredient and the benefit agent (104), in order to provide the user with a sensory awareness that the benefit agent (104) is being released onto the hair. Additionally, providing an extended release profile for a fragrance ingredient provides the hair with a pleasant smell that lasts longer than direct inclusion of the fragrance ingredient in the hair care composition (202).

In one example, a capsule (102) contains a benefit agent (104). The capsule (102) may be provided with an additional capsule (102) that contains a fragrance ingredient. In another example, the additional capsule (102) does not contain a benefit agent. Providing a capsule (102) containing a benefit agent (104) separately from a capsule (102) containing a fragrance may allow fine tuning of the ratio of a benefit agent (104) and a fragrance, whereby avoiding aggregation effects which may occur during capsule formation. Providing both a capsule (102) containing a benefit agent (104) and a capsule (102) containing a fragrance would produce a similar effect to a user as a capsule (102) that contains both a fragrance and a benefit agent (104).

A hair care composition (202) according to the present specification includes an encapsulated benefit agent (104). The capsule (102) that encapsulates the benefit agent (104) is discussed above. Suitable benefit agent (104) include moisturizing ingredients, conditioning ingredients, illuminating ingredients, and combinations thereof. A moisturizing ingredient may be any component that is capable of moisturizing the hair, and include occlusive-type moisturizers, oils, esters, humectants, and vitamins that may strengthen the hair to benefit the hair's natural moisture retention abilities. A conditioning ingredient may be any component that is capable of improving the moisture or feel of the hair, and include the aforementioned moisturizing ingredients, proteins, hydrolyzed proteins, cationic surfactants, and cationic polymers. Illuminating ingredients may be any component that provides a sparkling visual effect, and include mica, pearlescent pigments, and glitter particles. A benefit agent (104) may provide an amount of the weight of the capsule (102); in one example, a benefit agent (104) provides at least 50% of the weight of the capsule (102), relative to the total weight of the capsule (102). In another example, a benefit agent (104) provides at least 60%, such as at least 75% of the weight of the capsule (102), relative to the total weight of the capsule (102). In a further example, the benefit agent (104) provides at least 80%, such as at least 85% or at least 90% of the weight of the capsule (102), relative to the total weight of the capsule (102). In a further example, the benefit agent (104) provides at least 95%, such as at least 98% of the total weight of the capsule (102), relative to the total weight of the capsule (102).

Any occlusive-type moisturizing ingredient may be suitable for use as an encapsulated benefit agent (104) in a composition (202) according to the present specification. Examples of suitable occlusive-type moisturizing ingredients (104) include dimethicone and dimethicone-based polymers, such as amodimethicone, bis-PEG-12 dimethicone, and the like.

Any oil based moisturizing ingredient may be suitable for use as an encapsulated benefit agent (104) in a composition (202) according to the present specification. Oils are non-polar substances that are viscous liquids at room temperature (20-25° Celsius). Non-limiting examples of suitable oils include natural oils such as triglycerides and petroleum-derived hydrocarbons, synthetic oils such as hydrocarbons and silicones, and semi-synthetic oils such as hydrogenated or chemically modified triglycerides, as well as fatty alcohols. Non-limiting examples of specific oils which may be used in a composition (202) according to the present specification include coconut oil, palm oil, castor oil, meadowfoam seed oil, vegetable oil, animal fats such as tallow, hydrogenated analogs of the foregoing, cetyl alcohol, stearyl alcohol, paraffinum liquidum, and combinations and mixtures thereof.

Any ester-based moisturizing ingredient may be suitable for use as an encapsulated benefit agent (104) in a composition (202) according to the present specification. There may be some overlap between ester-based moisturizing ingredients and oil-based moisturizing ingredients. Non-limiting examples of suitable ester-based moisturizing ingredients include monoesters and polyesters, including triglyceride oils. Non-limiting examples of specific oils which may be used in a composition (202) according to the present specification include acetylated glycol stearate, arachidyl behenate, butyl avocadate, butyl myristate, cetearyl palmate, coco-caprylate, decyl oleate, dipentaerythrityl hexahydroxystearate, ethyl oleate, isocetyl myristate, propylene glycol stearate, diisopropyl adipate, polysorbates, and combinations and mixtures thereof.

Any humectant may be suitable for use as an encapsulated benefit agent (104) in a composition (202) according to the present specification. Humectants are hygroscopic substances that attract ambient moisture. Non-limiting examples of suitable humectants include glycerol, acetyl arginine, betaine, lauryl malamide, mannitol, propylene glycol, xylose, polymeric humectants such as lauryl methyl gluceth-10 hydroxypropyldimonium chloride, and combinations and mixtures thereof.

Any vitamins that strengthen the hair, whereby benefiting the hair's natural moisture retention abilities may be suitable for use as an encapsulated benefit agent (104) in a composition (202) according to the present specification. Other vitamins that may be suitable for use in a composition (202) according to the present specification are those that modulate hair rejuvenation or growth. For example, suitable vitamins include retinol (vitamin A), thiamine (vitamin $B_1$), riboflavin (vitamin $B_2$), niacin (vitamin $B_3$), pantothenic acid (vitamin $B_5$), pyridoxine (vitamin $B_6$), biotin (vitamin $B_7$), folic acid (vitamin $B_9$), cyanocobalamin (vitamin $B_{12}$), ascorbic acid (vitamin C), tocopherol (vitamin E), and combinations and derivatives thereof.

Any proteins that provide a conditioning effect to the hair, whereby benefiting the hair's appearance or feel may be suitable for use as an encapsulated benefit agent (104) in a composition (202) according to the present specification. Proteins are a natural polymers produced by cellular machinery; proteins are amino acid chains held together through amide bonds, and may include crosslinks, secondary, and/or tertiary structure as a result of the amino acids present, and the order of the amino acids in the protein. Proteins may also be modified, such as by attachment of sugars (glycosylation); such modification may occur enzymatically or chemically. Non-limiting examples of proteins which may be suitable for use as an encapsulated benefit agent (104) in a composition (202) according to the present specification include keratin, silk, wheat protein, glycoprotein, lactabumin, soy protein, collagen, and combinations thereof.

Any hydrolyzed protein that provides a conditioning effect to hair may be suitable for use as an encapsulated benefit agent (104) in a composition (202) according to the present specification. Hydrolyzed proteins are protein chains that have been cleaved along the amide backbone; hydrolysis may be enzymatic, acid-catalyzed, or base-catalyzed. Non-limiting examples of suitable hydrolyzed proteins that may be used as an encapsulated benefit agent (104) in a composition (202) according to the present specification include hydrolysis products of the above proteins.

Any cationic surfactant that is capable of conditioning the hair may be suitable for use as an encapsulated benefit agent (104) in a composition (202) according to the present specification. Cationic surfactants are compounds that have at least one hydrophobic region and at least one hydrophilic region. The hydrophobic region may interact with uncharged molecules, such as oils; the hydrophilic region may interact with polar components, such as water. Cationic surfactants also have a positive charge, which may be present in the hydrophilic region. Non-limiting examples of cationic surfactants which may be used as a benefit agent (104) in a composition (202) according to the present specification include cetrimonium chloride, behentrimonium chloride, steartrimonium chloride, stearalkonium chloride, dicetyldimonium chloride, distearyldimonium chloride, oleyl PG-trimonium chloride, and combinations thereof.

Any cationic polymer that is capable of conditioning the hair may be suitable for use as a benefit agent (104) in a composition (202) according to the present specification. Cationic polymers are polymers that contain positive charges in a monomeric unit. Non-limiting examples of cationic polymers which may be used as a benefit agent (104) in a composition (202) according to the present specification include the polyquaternium class of polymers, guar hydroxypropyltrimonium chloride, and combinations thereof.

Any mica that is capable of providing an optical effect may be suitable for use as a benefit agent (104) in a composition (202) according to the present specification. Micas are a class of phyllosilicate minerals. Non-limiting examples of micas which may be used as a benefit agent (104) in a composition (202) according to the present specification include muscovite, biotite, leipdolite, phlogopite, zinnwaldite, clintonite, illite, phengite, and combinations thereof.

Any pearlescent pigment that is capable of providing an optical effect on the hair may be suitable for use as a benefit agent (104) in a composition (202) according to the present specification. Pearlescent pigments are particulate pigments that have a shiny or glossy appearance. In some examples, pearlescent pigments provide different colors based on the angle of incident light and the angle of observation. Non-limiting examples of pearlescent pigments that may be used as a benefit agent (104) in a composition (202) according to the present specification include mica coated with metal oxides, aluminum oxide coated with metal oxides, bismuth oxychloride, and combinations thereof.

Any glitter particles that are capable of providing an optical effect on the hair may be suitable for use as a benefit agent (104) in a composition (202) according to the present specification. Glitter may be flat particles that reflect light at different angles, causing the particles to shimmer. Non-limiting examples of glitter particles that may be used as a benefit agent (104) in a composition according to the present specification include plastic-based glitters, glitter derived from stones such as malachite, glitter derived from natural sources such as insect-based glitters and glass-based glitters.

The capsule (102) containing a benefit agent (104) may be present in a composition (202) according to the present specification in an amount ranging from about 0.001% to about 50.00% by weight, relative to the total weight of the composition. In one example, the capsule (102) containing a benefit agent (104) is present in a composition (202) according to the present specification in an amount ranging from about 0.001% to about 20.00% by weight, such as from about 0.20% to about 10.00% by weight, or from about 1.00% to about 15.00% by weight, relative to the total weight of the composition. In another example, a capsule (102) containing a benefit agent (104) may be present in a composition (202) according to the present specification in an amount ranging from about 0.10% to about 20.00% by weight, such as from about 0.10% to about 2.00% by weight, or from about 5.00% to about 15.00% by weight, relative to the total weight of the composition.

A hair care composition (202) according to the present specification also includes a carrier. The carrier may be chosen based on the type of composition (202), and the intended use of the composition. For example, a carrier in a composition (202) according to the present specification may include water, ethanol, n-propanol, isopropanol, n-butanol, isobutanol, n-pentanol, 2-pentanol, 3-pentanol, polyethylene glycols such as PEG-4, PEG-6, PEG-8, PEG-10, and PEG-12, propylene glycol, polypropylene glycols such as PPG-3, PPG-6, PPG-9 and PPG-12, butylene glycol, polybutylene glycol, glycerol, petrolatum, paraffin, paraffinum liquidum, triglycerides, cetyl alcohol, stearyl alcohol, waxes, propellants such as n-butane and carbon dioxide, and combinations thereof. For example, water may be used as a carrier. In another example, a wax may be used as a carrier. In a further example, a capsule (102) may contain a carrier, which may be the same or different from the carrier in the hair care composition (202). In one such example, a capsule (102) contains water, and the carrier in the hair care composition (202) does not contain water.

A hair care composition (202) according to the present specification may include a carrier in any suitable amount, such as from about 5% to about 99.9% of the composition. For example, a hair care composition (202) according to the present specification may include from about 40% to about 99% by weight of a carrier, such as from about 50% to about 95% by weight of a carrier, relative to the total weight of the composition. In another example, a hair care composition (202) according to the present specification may include from about 10% to about 50% by weight, such as from about 15% to about 40% by weight of a carrier, relative to the total weight of the composition. In a further example, a hair care composition (202) according to the present specification may contain from about 65% to about 95% by weight, such as from about 75% to about 90% by weight of a carrier, relative to the total weight of the composition.

A hair care composition (202) according to the present specification may also include additional components. Such additional components may include a surfactant, a suspending polymer, a wax, a conditioning agent, an oil, a vitamin, a preservative, a fragrance, a deposition aid, and combinations thereof. A composition (202) according to the present specification may also contain additives known to an individual skilled in the art, such as a dye, a pigment, an antibacterial agent, a foaming agent, a plant extract, plant matter, a chelator, an alkali metal halide, and combinations thereof.

In one example, a composition (202) according to the present specification includes at least one surfactant. A surfactant has at least one hydrophobic end and at least one hydrophilic end. The hydrophobic end may allow the surfactant to interact with uncharged molecules, such as oils. The hydrophilic end may facilitate the interaction of the molecule with charged or polar molecules, such as water. The hydrophilic end may be used to classify surfactants, which may be anionic, cationic, nonionic, amphoteric, or zwitterionic. Anionic surfactants may have a negatively charged hydrophilic end. Examples of anionic surfactants include sulfate, sulfonate, carboxylate, phosphate, or the like. Anionic surfactants may be sensitive to water hardness. Cationic surfactants may be those that have a positively charged hydrophilic end, such as a quaternary amine. Non-ionic surfactants may have a hydrophilic end which may be charge neutral, such as an ethoxylate, glycoside, or poly-ol; such surfactants may not be sensitive to water hardness. Amphoteric surfactants may be those that have a hydrophilic end which has a functional group that is capable of acting as a base, and a functional group that is capable of acting as an acid, such as amine oxides. Zwitterionic surfactants may have both a positive and negative charge on their hydrophilic ends, such as sultaines, or betaines. The hydrophobic end may include a saturated or unsaturated, linear or branched, substituted or unsubstituted, cyclic or acyclic, alkyl or silyl chain containing at least 8 carbon or silicon atoms.

In one example, a composition (202) according to the present specification contains at least one surfactant, with a total concentration of surfactants being up to about 90% by weight, relative to the total weight of the composition. For example, a concentration of surfactants in a composition (202) according to the present specification may range from about 0.10% to about 50.00% by weight, or from about 0.20% to about 30.00% by weight, relative to the total weight of the composition. In a further example, a concentration of surfactants in a composition (202) according to the present specification may range from about 1% to about 20.00% by weight, such as from about 5.00% to about 15.00% by weight, relative to the total weight of the composition. In a still further example, a concentration of surfactants in a composition (202) according to the present specification is at least about 6.00% by weight, such as at least about 8.00% by weight, relative to the total weight of the composition. In another example, a concentration of surfactants in a composition (202) according to the present specification may range from about 10.00% to about 30.00% by weight, such as from about 15.00% to about 25.00% by weight, relative to the total weight of the composition.

A composition (202) according to the present specification may also include at least one suspending polymer. A suspending polymer may be added to suspend the capsules (102) containing a benefit agent (104) in the composition (202) according to the present specification. A suspending polymer may also be added as a viscosity modifier, to increase the viscosity of the composition (202) according to the present specification. Suspending polymers are a certain type of thickener, and may be a homopolymer or copolymer, which is capable of suspending at least one capsule (102) in solution. Non-limiting examples of suspending polymers include acrylate/C10-30 alkyl acrylate crosspolymer, acrylates copolymer, acrylates crosspolymer, acrylates crosspolymer-3, acrylates crosspolymer-4, carbomer, cellulose gum, polyacrylate crosspolymer-4, polyacrylate crosspolymer-6, polyacrylate crosspolymer-11, polyacrylate crosspolymer-14, polyacrylic acid, poly C10-30 alkyl acrylate, xanthan gum, guar gum, or combinations thereof. A suspending polymer may be present in a concentration ranging up to about 25% by weight, such as from about 0.01% to about 20% by weight, relative to the total weight of the composition. For example, a composition (202) according to the present specification may contain from about 0.1% to about 10% by weight, such as from about 0.5% to about 8% by weight of a suspending polymer. In another example, a composition (202) according to the present specification may contain from about 1% to about 10% by weight, such as from about 2% to about 6% by weight of a suspending polymer.

A composition (202) according to the present specification may also include at least one wax. A wax is a hydrophobic solid that is malleable at or near room temperature (20-25° Celsius). A wax may be included in a composition (202) according to the present specification as a carrier, viscosity modifier, hair styling agent, or adjuvant. A wax may be capable of shaping the hair, as well as acting as a moisturizing ingredient or conditioner due to its hydrophobic nature. Non-limiting examples of types of waxes include esters of fatty alcohols with fatty acids, sterol esters, and hydrocarbons. Non-limiting examples of waxes suitable for use in a composition (202) according to the present specification include beeswax, lanolin, sunflower seed wax, carnauba wax, montan wax, candelilla wax, paraffin wax, tallow tree wax, ceresin wax, and derivatives and combinations thereof. A composition (202) according to the present specification may contain any suitable quantity of wax, which may depend on the type of composition and the purpose that the wax serves in the composition. For example, where the wax is the carrier, the wax may provide from about 20% to about 99% by weight of the composition (202), such as from about 50% to about 90% by weight, or from about 60% to about 80% by weight, relative to the total weight of the composition. In another example, the wax is provided as a viscosity modifier or hair styling agent, and the wax may be included in a composition (202) according to the present specification at a concentration ranging from about 2% to about 40% by weight, such as from about 3% to about 30% by weight, or from about 3% to about 10% by weight, relative to the total weight of the composition (202). In a further example, the wax is provided as an adjuvant, and may be included in a composition (202) according to the present specification at a concentration ranging from about 0.01% to about 10% by weight, such as from about 0.1% to about 5% by weight, or from about 0.5 to about 2% by weight, relative to the total weight of the composition.

A composition (202) according to the present specification may also contain a number of conditioning agents. Conditioning agents may be components which act to preserve existing moisture by creating a hydrophobic barrier between the moisturized hair or skin of the scalp and the air, and may be incorporated into an example of compositions (202) according to the present specification for this purpose. Non-limiting examples of conditioning agents include the polyquaternium class of polymers, proteins, hydrolyzed proteins, quaternary amine cationic surfactants, fatty alcohols and polyols. A composition (202) according to the present specification may contain any suitable amount of conditioning agent, such as up to about 40% by weight, relative to the total weight of the composition. For example, a composition (202) according to the present specification may contain from about 2% to about 30% by weight, or from about 4% to about 20% by weight of a conditioning agent. In another example, a composition (202) according to the present specification may contain from about 1% to about 10% by weight, such as from about 2% to about 5% by weight of a conditioning agent, relative to the total weight of the composition (202).

A composition (202) according to the present specification may also contain an oil. For the purposes of the present specification, oil is taken to include both hydrocarbon-based oils and silicone-based oils. Oils are neutral, nonpolar substances that are viscous liquids at ambient temperature and pressure (1 atmosphere pressure, 20-25° Celsius). Oils may be included in a composition (202) according to the present specification in order to act as conditioning agents, or to replenish natural oils on the scalp or hair. Oils include triglycerides, fatty alcohols, mineral oils, and silicone oils. Examples of oils that may be suitable for use in a composition (202) according to the present specification include olive oil, rapeseed oil, paraffinum liquidum, cetyl alcohol, stearyl alcohol, oleyl alcohol, soybean oil, dimethicone, cyclomethicone, PEG-12 dimethicone, amodimethicone, alkyl methicones, and derivatives and combinations thereof. A composition (202) according to the present specification may contain an oil in any suitable amount, such as up to about 20% by weight, relative to the total weight of the composition. For example, a composition (202) according to the present specification may contain from about 0.1% to about 15% by weight, such as from about 1% to about 10% by weight of an oil, relative to the total weight of the composition. In another example, a composition (202) according to the present specification may contain from about 0.1% to about 5% by weight, or from about 8% to about 15% by weight of an oil, relative to the total weight of the composition.

A composition (202) according to the present specification may also contain a number of vitamins. Vitamins are organic compounds that an organism requires in limited quantities, and which the organism that uses the vitamin cannot synthesize from other precursors. Vitamins, or vitamin derivatives, may be included in an example of a composition (202) according to the present specification as conditioning agents, preservatives, antioxidants, or to improve consumer acceptance of the composition. Non-limiting examples of vitamins include retinol (vitamin A), thiamine (vitamin $B_1$), riboflavin (vitamin $B_2$), niacin (vitamin $B_3$), pantothenic acid (vitamin $B_5$), pyridoxine (vitamin $B_6$), biotin (vitamin $B_7$), folic acid (vitamin $B_9$), cyanocobalamin (vitamin $B_{12}$), ascorbic acid (vitamin C), tocopherol (vitamin E), and phylloquinone (vitamin K). For the purposes of the present specification, "vitamin" also includes derivatives and stereoisomers of vitamins, such as tocopheryl acetate, polyoxypropylene (2) polyoxyethylene (5) tocopherol ether, and isoascorbic acid. A composition (202) according to the present specification may contain up to about 10% vitamins in the bulk composition, separate from any vitamins that may be present in the capsules (102) as or with the benefit agent (104). For example, a composition (202) according to the present specification may contain from about 0.01% to about 7% by weight, such as from about 0.1% to about 5% by weight of vitamins, relative to the total weight of the composition.

A composition (202) according to the present specification may also contain a number of preservatives. Preservatives are compounds that are added to composition (202) according to the present specification to prevent undesirable decomposition over time. Non-limiting examples of preservatives include benzoic acid, benzyl alcohol, phenol, phenoxyethanol, formaldehyde, glyoxal, DMDM hydantoin, cresol, para-hydroxybenzoic acid and esters thereof, chlorhexidine, propionic acid, and salts and/or combinations thereof. A composition (202) according to the present specification may contain up to 5% by weight about of preservatives, relative to the total weight of the composition. For example, a composition according to the present specification may contain from about 0.01% to about 3%, such as from about 0.05% to about 2% of preservatives, relative to the total weight of the composition.

A composition (202) according to the present specification may also contain a fragrance. A fragrance comprises a number of ingredients; fragrance ingredients are compounds that provide the composition with a pleasing scent. While fragrances may often be complex mixtures of fragrance ingredients, it is also possible to include a single fragrance ingredient in a composition (202) according to the present specification. The olfactory intensity of a fragrance ingredient may be a function of the concentration of the fragrance ingredient, the vapor pressure of the fragrance ingredient, and the potency of the interactions between the fragrance ingredient and a user's olfactory receptors. A fragrance may be incorporated into the capsules (102) along with the benefit agent (104) in order to provide a user with a sensory awareness that the moisturizing ingredient (104) has been deployed onto the hair. Alternatively, a fragrance may also be incorporated into the composition (202) directly. A composition (202) according to the present specification may also incorporate a fragrance both into the capsules (102) containing the benefit agent (104), as well as in the composition itself; the fragrance incorporated into the capsules may either the same as, or different from, the fragrance in the bulk composition (202) according to the present specification.

Fragrance ingredients are generally known by an individual skilled in the art, and include ketones, aldehydes, esters, and the like. Fragrance ingredients also include naturally-occurring plant and animal oils. Non-limiting examples of suitable fragrance ingredients include linalool, hexyl salicylate, citronellol, butylphenyl methylpropional, limonene, allylanisole, carvone, nonalactone, liffarome, 2,4-dimethyl-3-cyclohexene carboxaldehyde, adoxal, galaxolide, methyl benzoate, geraniol, camphor, citral, eucalyptol, alpha-damascone, florhydral, and the like. Derivatives and combinations thereof may also be suitable for use in a composition (202) according to the present specification.

A composition (202) according to the present specification may contain a fragrance in an amount of up to about 10% by weight, such as from about 0.001% to about 5% by weight, relative to the weight of the total composition. For example, a composition (202) according to the present specification may contain a fragrance in an amount of from about 0.01% to about 4% by weight, or from about 0.05% to about 2% by weight, relative to the total weight of the composition.

A composition (202) according to the present specification may also include a deposition aid. A deposition aid may be a compound or macromolecular structure that assists in the deposition of the capsule (102) containing a benefit agent (104) onto the hair shaft or the scalp of a user. Because the hair and skin may be negatively charged, the deposition aid may be positively charged. In another example, the deposition aid is uncharged. In still another example, the deposition aid is zwitterionic. Deposition aids may come in a variety of forms, including cationic polymers, cationic surfactants, and agents that promote deposition by a reversible or irreversible tethering mechanism. In one example, a deposition aid is selected from cationic polymers, such as polyquaternium-7, polyquaternium-10, polyquaternium-11, and the like. In another example, a deposition aid is attached to the surface of the capsule (102), either as part of a polymerization reaction in encapsulation or as a later step after polymerization; such an attachment to the surface of the capsule may be by any suitable bond, such as an ester, ether, amide, imide, urethane, and the like. The end of the deposition aid not attached to the capsule (102) may be designed to either adhere to the keratin fibers of the hair through charge-charge interactions or by reaction with exposed functional groups on the surface of the keratin. A deposition aid may be present in a composition (202) according to the present specification in any suitable amount, such as up to about 20% by weight, relative to the total weight of the composition. In one example, a composition (202) according to the present specification contains from about 0.001% to about 15% by weight, such as from about 0.01% to about 10% by weight of a deposition aid, relative to the total weight of the composition. In another example, a composition (202) according to the present specification contains from about 0.1% to about 10% by weight, such as from about 0.1% to about 5% by weight of a deposition aid, relative to the total weight of the composition.

Dyes and pigments are compounds which confer color to a composition (202) or to the hair to which a dye or pigment is applied. Dyes and pigments may be added to an example of a composition (202) according to the present specification in order to imbue the composition with a consumer-acceptable color. In another example, a dye or pigment is added to a composition (202) according to the present specification in order to provide a simultaneous coloring effect to the hair. Non-limiting examples of dyes and pigments which may be used to color the composition (202) according to the present specification include titanium dioxide, mica, iron oxides, violet 2, red 4, red 6, red 7, red 33, red 40, blue 1, blue 4, yellow 5, yellow 6, yellow 10, orange 4, orange 5, orange 10, vat red 1, vat blue 1, vat blue 4, vat blue 6, vat orange 7, vat violet 2, and combinations thereof.

Dyes and pigments may also include permanent dyes, and direct dyes, which may be either semi-permanent dyes or temporary dyes. Permanent dyes may include oxidative dye precursors, which react with oxidizing agents, such as hydrogen peroxide, to form dye molecules on the hair. Oxidative dye precursors include oxidation bases, which include para- and ortho-substituted aromatic rings; these may be supplemented by couplers, which modify the color produced by the oxidation dye precursors, and include meta-substituted aromatic rings. Semi-permanent dyes include anthraquinones, other multicyclic ring systems, as well as monocyclic compounds that confer color directly, such as 4-amino-3-nitrophenol. Temporary hair dyes confer color to the hair only until the hair is washed, and include inorganic pigments comprising titanium dioxide, mica, iron oxides, and/or ultramarines, as well as cationic dyes such as basic blue 99 and basic brown 17. Dyes and pigments may be used in any suitable quantity, including up to about 20% by weight, relative to the total weight of the composition. For example, a composition according to the present specification may contain from about 1% to about 20% by weight, such as from about 4% to about 15% by weight of dyes and/or pigments, relative to the total weight of the composition. In one example in which the composition (202) contains a number of permanent dyes, the composition may also be mixed with another composition containing from about 2% to about 30% by weight, such as from about 6% to about 20% of an oxidant, such as hydrogen peroxide.

A composition (202) according to the present specification may also include at least one antibacterial agent. An antibacterial agent is any agent that assists in the removal of bacteria, kills bacteria, or arrests bacterial growth. Some antibacterial agents also have additional functions, and belong to one or more than one of the aforementioned or following classes. Suitable non-limiting examples of antibacterial agents include antiseptics, triclosan, triclocarban, usnic acid salts, benzethonium salts, benzalkonium salts, compounds which inhibit the 70S (bacterial) ribosome, and compounds which reduce the integrity of the bacterial cell wall. Additional non-limiting examples of antibacterial agents include ethanol, isopropanol, aminoglycosides (such as neomycin), cephalosporins (such as cefalexin), lincosamides (such as lincomycin), tetracyclines (such as doxycycline), penicillins (such as amoxicillin), and combinations thereof. A composition (202) according to the present specification may contain an antibacterial agent in any appropriate amount, such as from about 0.1% to about 75% by weight. Antibacterial agents such as ethanol and isopropanol may require higher concentrations, such as from about 50% to about 75%, and may also provide the carrier for the composition (202) according to the present specification. In contrast, antibacterial active ingredients such as benzethonium and benzalkonium salts may be effective at lower concentrations, such as from about 0.1% to about 10% by weight, or from about 1% to about 6% by weight, relative to the total weight of the composition.

Foaming agents are compounds that stabilize foams. Foaming agents increase the propensity of a composition (202) according to the present specification to form a foam, and/or may stabilize a foam by inhibiting the coalescence of bubbles within the foam. Certain types of surfactants are capable of acting as foaming agents in a composition (202) according to the present specification; however, not every type of surfactant enhances foam stability. Non-limiting examples of foaming agents include sodium laureth sulfate, cocamidopropyl betaine, cocamidopropyl hydroxysultaine, behenyl betaine, hydroxystearamide MEA, lauramide MEA, myristamide MEA, myristamide DEA, PEG-3 lauramide, PEG-2 lauramine, lauramine oxide, PEG-3 lauramine oxide, and cocamine oxide. A number of foaming agents may be included in a composition according to the present specification at concentrations up to about 10% by weight, such as from about 0.1% to about 7% by weight, or from about 0.5% to about 5% by weight, relative to the total weight of the composition.

Plant extracts are natural compounds or mixtures of compounds produced in a plant that contain at least one agent that has either a real or perceived benefit to the skin, or to the composition as a whole. The inclusion of some plant extracts may improve consumer acceptance of a composition (202) according to the present specification on the basis of these benefits, or a consumer preference for naturally produced compositions over synthetically produced compositions. Plant extracts include oils, fragrance ingredients, fatty acids, and/or various other components depending on the extraction methods employed and any subsequent processing that is performed. Non-limiting examples of plant extracts include *Prunus Amygdalus dulcis* extract, *Oenothera biennis* extract, *Zingiber officinale* extract, *Jasminum* extracts, *Lavandula angustifolia* extract, *Mentha x piperita* extract, *Rosa* extracts, *Hypericum perforatum* extract, and combinations thereof. A composition (202) according to the present specification may contain up to about 20% by weight, such as from about 0.1% to about 15% by weight, or from about 0.5% to about 10% by weight of plant extracts, relative to the total weight of the composition.

Plant matter is plant material which may be incorporated into an example of compositions (202) according to the present specification. Such plant material may provide abrasive properties as exfoliants, fragrance properties, or may be able to act as a thickener. The incorporation of plant matter into a composition (202) according to the present specification may improve consumer acceptance, which may be based on the perception of the natural qualities of the compositions including plant matter. Non-limiting examples of plant matter which may be incorporated in compositions according to the present specification include whole flowers, flower petals, stems, seeds, roots, and fruits.

Chelators are compounds that coordinate metal ions. Chelators may be included in an example of a composition (202) according to the present specification as antibacterial agents, preservatives, pH regulators, or to provide other such properties to the composition. Non-limiting examples of chelators include natural polyacids (such as citric acid), phosphate salts (such as disodium pyrophosphate), bisphosphonates (such as etidronic acid), aminocarboxylic acids (such as ethylenediaminetetraacetic acid (EDTA) and ethylenediamine-N,N'-disuccinic acid (EDDS)), and combinations and/or salts thereof. Chelators may be included in a composition (202) according to the present specification in any suitable amount, such as up to about 5% by weight, relative to the total weight of the composition.

Alkali metal halides are salts of alkali metals and halogen atoms. Alkali metal halides may be included in an example of a composition (202) according to the present specification as thickeners, ionic strength modulators, or to confer other such properties to the composition. Alkali metal halides are neutral compounds. Non-limiting examples of alkali metal halides include lithium chloride, lithium bromide, sodium chloride, sodium bromide, potassium chloride, potassium bromide, and combinations thereof. A composition (202) according to the present specification may contain an alkali metal halide in any suitable amount, such as up to about 5% by weight, relative to the total weight of the composition.

A composition (202) according to the present specification may also contain other, additional components known to an individual skilled in the art. For example, a composition (202) according to the present specification may contain additional polymers, which may be natural, synthetic, and/or semi-synthetic. Natural polymers include hydrolyzed keratin, silk, collagen, honey, cellulose, and the like. Synthetic polymers include acrylates/acrylamide copolymers, acrylamidopropyltrimonium chloride/acrylates copolymers, polyethylene glycol polymers, polypropylene glycol polymers, polyquaterniums, and the like. Semi-synthetic polymers include chemically modified natural polymers, polymers assembled from both natural and synthetic monomers, and the like. In another example, a composition (202) according to the present specification includes an exfoliant, which are particles that do not dissolve in the carrier and act as an abrasive to assist in efficient cleansing of the hair. In a further example, a composition (202) according to the present specification includes a pH buffer, to maintain the pH within a desired range. In another example, the composition (202) includes a pH adjusting agent, which may be provided either with or without a pH buffer. In yet another example, a composition (202) according to the present specification includes an enzyme. In a further example, the composition (202) according to the present specification may contain a UV stabilizer or protectant which may reduce damage to the hair resulting from exposure to the sun. In another example, the composition (202) according to the present specification may contain a bleaching agent.

A composition (202) according to the present specification may have any suitable viscosity, and may be a liquid, solid or semi-solid. Viscosity of compositions (202) according to the present specification may be measured in centipoise (cps). A composition (202) according to the present specification may have a viscosity in the range of about 0.8 cps to about 500,000 cps. According to one example, a composition (202) according to the present specification is prepared and offered in a container that foams the composition (202) concurrently with dispensing the composition, and the composition has a viscosity in the range of about 0.8 cps to about 1,000 cps, such as from about 5 cps to about 100 cps. In another example, a composition (202) according to the present specification is not subjected to a foaming operation upon dispensing, and is offered as a liquid with a viscosity in the range of about 1,000 to about 5,000 cps, such as from about 2,000 cps to about 4,000 cps. In another example, a composition (202) according to the present specification is dispensed in a tub or jar as a solid or semi-solid, and has a viscosity in the range of about 10,000 cps to about 500,000 cps, such as from about 50,000 cps to about 300,000 cps.

Methods

The present specification is also directed to a method (300) for using a composition (202) according to the present specification. The method (300) includes applying (301) the hair care composition (202) comprising an encapsulated benefit agent (104) to the hair. The method (300) additionally includes touching or rubbing (302) the hair to open capsules (102) containing the encapsulated benefit agent (104). The method (300) also includes depositing (303) the moisturizing ingredient (104) onto the hair.

The method (300) for using a composition (202) according to the present specification may also include additional, optional steps. In one example, such steps may include lathering the hair with the composition (202), rinsing the composition (202) from the hair, partially rinsing the composition (202) from the hair, air drying the hair, drying the hair using heat, styling the hair, and any other suitable step that is known to an individual skilled in the art of hair treatment.

The present specification is also directed to a method (400) for preparing a composition (202) according to the present specification. The method (400) includes preparing (401) an aqueous slurry that contains a benefit agent (104) to be encapsulated. The method (400) also includes forming (402) polymeric capsules in the aqueous slurry around the benefit agent (104).

The method (400) for making a composition (202) according to the present specification may also include additional, optional steps. According to one example, such steps may include isolation of the capsules from the aqueous slurry of benefit agent (104), such as by filtration. If the capsules are isolated, the isolated capsules may then be incorporated into a hair care composition (202) according to the present specification to provide a composition (202) that includes a capsule (102) that contains an encapsulated benefit agent (104). In another example, such steps may include addition of other ingredients to prepare the composition (202) according to the present specification directly from the slurry. In such an example, the aqueous slurry that includes the capsules (102) that contain the encapsulated moisturizing ingredient (104) provides the base for the hair care composition (202) according to the present specification. Each of the above examples may be appropriate for certain types of hair care compositions (202) according to the present specification. For example, a hair wax composition (202) may contain a small enough proportion of water that the capsules (102) containing the encapsulated benefit agent (104) may be isolated prior to incorporation into the composition (202) according to the present specification. In another example, a conditioner composition (202) according to the present specification may be prepared from the aqueous slurry directly, by addition of other components of the conditioner composition (202); any benefit agent (104) that was not encapsulated could be used to provide an immediate benefit to the hair, and the encapsulated benefit agent (104) would provide the same benefit agent (104) to the hair after the hair has dried.

Additionally, if the capsules (102) containing an encapsulated benefit agent (104) according to the present specification are modified by a tethered deposition aid, then the method (400) of preparing a composition (202) according to the present specification may further include a tethering operation. Such a tethering operation may be accomplished by any suitable means, and may involve a number of chemical reactions that result in the tethering of a deposition aid onto the surface of a capsule (102) according to the present specification.

EXAMPLES

In the following examples, all amounts are percentages by weight unless indicated otherwise.

Example 1: Shampoo

TABLE (I)

| Component | Example Compound | Concentration |
| --- | --- | --- |
| Glycerin | Glycerin | 0.50-2.00 |
| Zwitterionic Surfactant | Cocamidopropyl Betaine | 1.50-4.50 |
| Anionic Surfactant | Sodium Laureth Sulfate | 8.00-12.00 |
| Preservatives | DMDM Hydantoin | 0.02-0.09 |
| Chelator | Tetrasodium EDTA | 0.01-0.05 |
| Cationic Polymer | Polyquaternium-7 | 0.09-0.20 |
| Suspending Aid | Acrylates Copolymer | 2.10-2.80 |
| pH Adjusting Agent | Sodium Hydroxide | 0.227-0.302 |
| Pearlescent Pigment | Timiron Supersheen MP-1001 (Titanium dioxide coated mica) | 0.02-0.40 |
| Pearlizing Agents | Glycol Distearate and Steareth-4 | 0.95-2.50 |
| Fragrance | Fragrance Mixture | 0.50-1.50 |
| Alkali Metal Halide | Sodium Chloride | 0.10-0.75 |
| Encapsulated Benefit Agent | Caprylic/Capric Triglyceride and Polyquaternium-6 encapsulated in Hexamethylenediamine/MDI Copolymer | 1.50-3.20 |
| Water | Water | q.s. to 100 |

In Table I, a formulation composition for a shampoo is provided. The formulation was prepared by preparation of the encapsulated benefit agent, which was then added to a mixture of the remaining shampoo composition components. Example 1 produces a shampoo composition with a pearlescent appearance, effective cleansing of the hair, and lasting moisturizing benefits, which may be attributable to the encapsulated benefit agent.

Example 2: Conditioner

TABLE (II)

| Component | Example Compound | Concentration |
| --- | --- | --- |
| Glycerin | Glycerin | 1.50-5.00 |
| Preservative | Methylparaben | 0.15-0.30 |
| Preservative | Phenoxyethanol | 0.45-0.75 |
| Conditioning Agent | Stearalkonium Chloride | 1.00-2.50 |
| Conditioning Agent | Behentrimonium Chloride | 0.85-2.90 |
| Conditioning Agent | Ethylhexyl Palmitate | 0.20-1.20 |
| Conditioning Agent | Dimethicone | 1.00-3.00 |
| Viscosity Modifier | Cetearyl Alcohol | 1.50-4.50 |
| Viscosity Modifier | Cetyl Alcohol | 2.50-5.00 |
| Fragrance | Fragrance Mixture | 0.20-0.95 |
| Encapsulated Benefit Agent | Caprylic/Capric Triglyceride and Polyquaternium-6 encapsulated in Hexamethylenediamine/MDI Copolymer | 1.50-3.20 |
| Water | Water | q.s. to 100 |

In Table II, a formulation for a conditioner is provided. The formulation was prepared by preparation of the encapsulated benefit agent, which was then added to a mixture of the other conditioner composition components. Example 2 provides a conditioner that provides effective conditioning benefit to the hair, and provides the hair with lasting moisture which may be attributable to the encapsulated benefit agent.

Example 3: Leave-on Repair Spray

TABLE (III)

| Component | Example Compound | Concentration |
| --- | --- | --- |
| Glycerin | Glycerin | 0.001-10.00 |
| Nonionic Surfactant | PEG-7 Glyceryl Cocoate | 0.10-5.00 |
| Humectant | Lactic Acid | 0.01-1.00 |
| Silicone | Dimethicone | 5.00-40.00 |
| Conditioning Agent | Stearamidopropyl Dimethylamine | 0.10-3.00 |
| Conditioning Agent | Panthenol | 0.01-10.00 |
| Conditioning Agent | Cetrimonium Chloride | 0.10-5.00 |
| Fragrance | Fragrance Mixture | 0.20-0.95 |
| Preservative | Phenoxyethanol | 0.10-0.90 |
| Encapsulated Benefit Agent | Caprylic/Capric Triglyceride and Polyquaternium-6 encapsulated | 1.00-5.00 |

TABLE (III)-continued

| Component | Example Compound | Concentration |
|---|---|---|
| | in Hexamethylenediamine/MDI Copolymer | |
| Alcohol | Ethanol | 13.00-30.00 |
| Water | Water | q.s. to 100 |

In Table III, a formulation for a leave-on repair spray is provided. The formulation was prepared by preparation of the encapsulated benefit agent, which was then added to a mixture of the other leave-on repair spray composition components. Example 3 provides a hair spray that provides effective conditioning benefit to the hair, and provides the hair with lasting moisture which may be attributable to the encapsulated benefit agent.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A hair care composition, comprising: at least one surfactant selected from anionic, nonionic, zwitterionic and amphoteric surfactants;
at least one capsule, wherein the at least one capsule encapsulates a benefit agent, and the benefit agent provides at least 85% of the weight of the capsule; and
a carrier,
wherein the at least one capsule comprises a shell of hexamethylenediamine/methylenediphenyl diisocyanate copolymer.

2. The hair care composition of claim 1, further comprising at least one additional capsule that encapsulates a fragrance ingredient.

3. The hair care composition of claim 1, in which the at least one capsule becomes more brittle when the surrounding environment is dry.

4. The hair care composition of claim 1, in which the at least one capsule releases the encapsulated benefit agent onto the hair in response to abrasion.

5. The hair care composition of claim 1, in which the at least one surfactant provides at least 6% by weight of the hair care composition, relative to the total weight of the composition.

6. The hair care composition of claim 1, in which the carrier is water.

7. The hair care composition of claim 1, in which the at least one capsule that encapsulates a benefit agent has a size ranging from about 5 micrometers (μm) to about 75 μm.

8. The hair care composition of claim 7, in which the at least one capsule that encapsulates a benefit agent has a size ranging from about 10 μm to about 50 μm.

9. The hair care composition of claim 1, in which the benefit agent is the only component encapsulated by the at least one capsule.

10. The hair care composition of claim 1, in which the benefit agent comprises an agent selected from oils, esters, oil soluble vitamins.

11. The hair care composition of claim 1, in which the at least one capsule is present in the composition at a concentration ranging from about 0.001% to 20.00% by weight.

12. The hair care composition of claim 11, in which the at least one capsule is present in the composition at a concentration ranging from about 0.10% to about 2.00% by weight.

13. The hair care composition of claim 1, further comprising a suspending polymer.

14. The hair care composition of claim 1, wherein the benefit agent comprises a triglyceride.

15. A hair care composition, comprising: at least one surfactant selected from anionic, nonionic, zwitterionic and amphoteric surfactants;
at least one capsule, wherein the at least one capsule encapsulates a benefit agent, and the benefit agent provides at least 85% of the weight of the capsule; and
a carrier,
wherein the at least one capsule comprises a shell of guanidine carbonate/hexamethylene diisocyanate isocyanurate trimer/methylenediphenyl diisocyanate crosspolymer.

* * * * *